(12) United States Patent
Stone

(10) Patent No.: US 7,594,934 B2
(45) Date of Patent: Sep. 29, 2009

(54) GALACTOSIDASE-TREATED PROSTHETIC DEVICES

(75) Inventor: Kevin R. Stone, Mill Valley, CA (US)

(73) Assignee: Crosscart, Inc., San Francisco, CA (US)

( * ) Notice: Subject to any disclaimer, the term of this patent is extended or adjusted under 35 U.S.C. 154(b) by 507 days.

(21) Appl. No.: 10/517,863

(22) PCT Filed: Jun. 4, 2003

(86) PCT No.: PCT/US03/17444

§ 371 (c)(1),
(2), (4) Date: Jun. 6, 2005

(87) PCT Pub. No.: WO03/105737

PCT Pub. Date: Dec. 24, 2003

(65) Prior Publication Data

US 2005/0221703 A1 Oct. 6, 2005

(51) Int. Cl.
*A61F 2/36* (2006.01)
*A61F 2/38* (2006.01)
(52) U.S. Cl. .............. 623/23.72; 623/11.11; 623/23.76
(58) Field of Classification Search .............. 623/13.17, 623/16.11, 23.61–23.64, 23.72–23.76; 424/422, 424/423

See application file for complete search history.

(56) References Cited

U.S. PATENT DOCUMENTS

| 4,880,429 | A | * | 11/1989 | Stone ........................ 623/14.12 |
| 5,108,438 | A | * | 4/1992 | Stone ........................ 623/17.16 |
| 5,116,374 | A | * | 5/1992 | Stone ........................... 435/325 |
| 5,984,858 | A | * | 11/1999 | Stone ........................... 600/20 |
| 6,046,379 | A | * | 4/2000 | Stone et al. ............... 623/14.12 |
| 6,231,608 | B1 | * | 5/2001 | Stone ........................ 623/16.11 |

FOREIGN PATENT DOCUMENTS

WO    WO 00/47132    8/2000

\* cited by examiner

*Primary Examiner*—Suzette J Gherbi
(74) *Attorney, Agent, or Firm*—John M. Garvey; Matthew L. Fenselau; Foley & Lardner LLP

(57) ABSTRACT

Matrix material for a substantially immunologically-compatible meniscal augmentation device of biocompatible and partially bioresorbable fibers is prepared by treatment with oc-galactosidase to eliminate oc-Gal epitopes. Upon implantation into a segmental defect of a meniscus, the composite of the meniscal augmentation device and the meniscus establishes a scaffold adapted for ingrowth of meniscal fibrochondrocytes.

7 Claims, 7 Drawing Sheets

GALACTOSIDASE-TREATED PROSTHETIC DEVICES

FIELD OF THE INVENTION

The invention relates to implantable prosthetic devices, and more particularly to the regeneration of tissue using substantially immunologically-compatible devices as in vivo scaffolds.

BACKGROUND OF THE INVENTION

The medial and lateral menisci are biconcave, generally C-shaped wedges of fibrocartilage interposed between the condyles of the femur and the tibia. Together, the menisci act as crucial stabilizers, providing a mechanism for force distribution, and a lubricant between the tibia and the femur. Without functional menisci, stress concentration occurs in the knee in conjunction with abnormal joint mechanics. These phenomena can result in premature development of arthritis.

The replacement of meniscal tissue with structures consisting of permanent artificial materials, however, is often unsuccessful. This lack of success is due principally to the fact that opposing articular cartilage of human and animal knee joints is fragile. The articular cartilage in the knee joint will not withstand abrasive interfaces, or compliance variances from normal, which eventually result from implanted artificial prosthetic menisci. In addition, joint forces are multiples of body weight that, in the case of the knee and hip, are typically encountered over a million cycles per year. Thus far, permanent artificial menisci have not been composed of materials having natural meniscal properties, nor have they been able to be positioned securely enough to withstand such routine forces.

U.S. Pat. Nos. 6,042,610, 5,735,903, 5,479,033, 5,624,463, 5,306,311, 5,108,438, 5,007,934, and 4,880,429 (each incorporated herein by reference) describe a prosthetic meniscus comprising biocompatible fibers, such as natural polymers, and methods for fabricating such prosthetic menisci. These patents also describe methods of regenerating meniscal tissue by implanting the prosthetic meniscus into a human knee. These patents generally disclose prosthetic menisci formulated from dry, porous matrices of processed natural fibers such as reconstituted cross-linked collagen, which optionally include glycosaminoglycan molecules. Generally, the source of collagen for these prosthetic menisci has been animal Achilles tendons or skin. The reconstitution process removes non-collagenous materials such as glycoproteins, proteoglycans, lipids, native glycosaminoglycans, and the like, which may confer additional elastic properties to the original tissue. However, the reconstitution process can leave antigenic components, causing an immunological reaction when the prosthetic meniscus is implanted into a subject.

Accordingly, there is a continuing need in the art for a substantially immunologically-compatible prosthetic meniscus.

SUMMARY OF THE INVENTION

The invention provides a substantially immunologically-compatible meniscal augmentation device for implantation into a subject, in a region disposed between and connecting two of the subject's bones. The region can be a segmental defect of a meniscus, an intervertebral region, a ligament region, or other area. The subject can be a human. The implantable prosthetic device has a reduced immunogenicity, due to the treatment of the matrix material from which the device is constructed. The matrix material is treated with $\alpha$-galactosidase to eliminate $\alpha$-Gal epitopes.

Upon implantation into the region disposed between and connecting two of the subject's bones, the composite formed by the subject's body region and the device has an in vivo outer surface contour substantially the same as a natural region that is being treated. The device establishes a biocompatible and partially bioresorbable scaffold adapted for ingrowth of fibrochondrocytes, fibroblasts or chondrocytes (such as meniscal fibrochondrocytes, vertebral fibrochondrocytes, etc.). The scaffold, together with the ingrown cells support natural load forces in the region.

The invention also provides methods for fabricating a prosthetic device having in vivo the shape desired (such as a segmental defect in a meniscus, for example). The method involves preparing matrix material by treatment with $\alpha$-galactosidase to eliminate $\alpha$-Gal epitopes. The method also involves placing a plurality of the resulting biocompatible and partially bioresorbable fibers into a mold defining the desired shape, lyophilizing the fibers, and contacting the fibers with a chemical cross-linking agent such that the fibers assume the shape of the mold. The mold defines the outer surface of the device to complement the desired body region.

Alternatively, after the molding is completed, the structure or matrix formed in the mold is cut so that its outer surface is complementary to a segmental defect. This method yields a matrix adapted to have an outer surface contour complementary to that of the segmental defect in the meniscus. When implanted into the segmental defect of the meniscus, the matrix establishes a biocompatible and an at least partially bioresorbable scaffold for ingrowth of meniscal fibrochondrocytes and for supporting natural meniscal load forces. The in vivo outer surface of the composite of the meniscus and the implanted matrix is substantially the same as that of a natural meniscus without segmental defect.

In addition, the invention provides a method for regenerating meniscal tissue in vivo. The method involves fabricating a meniscal augmentation device composed of biocompatible and at least partially bioresorbable fibers with reduced immunogenicity as described above, and then implanting the device into a segmental defect in the meniscus. This implanted device establishes a biocompatible and an at least partially bioresorbable scaffold adapted for ingrowth of meniscal fibrochondrocytes. The scaffold in combination with the ingrown meniscal fibrochondrocytes support natural meniscal load forces.

In another embodiment, the invention provides a method of preparing a prosthetic device, which includes removing at least a portion of a tissue from a non-human animal to provide matrix material; washing the matrix material in water and alcohol; subjecting the matrix material to a cellular disruption treatment; and digesting the matrix material with a glycosidase to remove first surface carbohydrate moieties, then preparing the matrix material as a prosthetic device, as described above.

In yet another embodiment, the invention provides a prosthetic meniscus for implantation into a subject that includes a device wherein the matrix material is made from a portion of a soft tissue from a non-human animal, wherein the portion includes extracellular components and substantially only dead cells, the extracellular components and dead cells having substantially no surface $\alpha$-galactosyl moieties. The prosthetic device is substantially non-immunogenic. Optionally, the material has capping molecules linked to at least a portion of surface carbohydrate moieties, or has reduced proteoglycans.

DETAILED DESCRIPTION OF THE INVENTION

A prosthetic device fabricated from biocompatible and bioresorbable fibers can be surgically implanted into a region disposed between and connecting two of the subject's bones, so as to provide normal motion and strength (for surgical implantation, see, U.S. Pat. Nos. 6,042,610, 5,735,903, 5,479,033, 5,624,463, 5,306,311, 5,108,438, 5,007,934, and 4,880,429, each incorporated herein by reference). The prosthetic device also acts as a scaffold for regenerating tissue, the ingrowth of which is encouraged by the physical characteristics of the implanted device. Such ingrowth results in a composite of the subject host body region and the prosthetic device that has an in vivo outer surface contour that is substantially the same as a natural body region.

Figure 1:
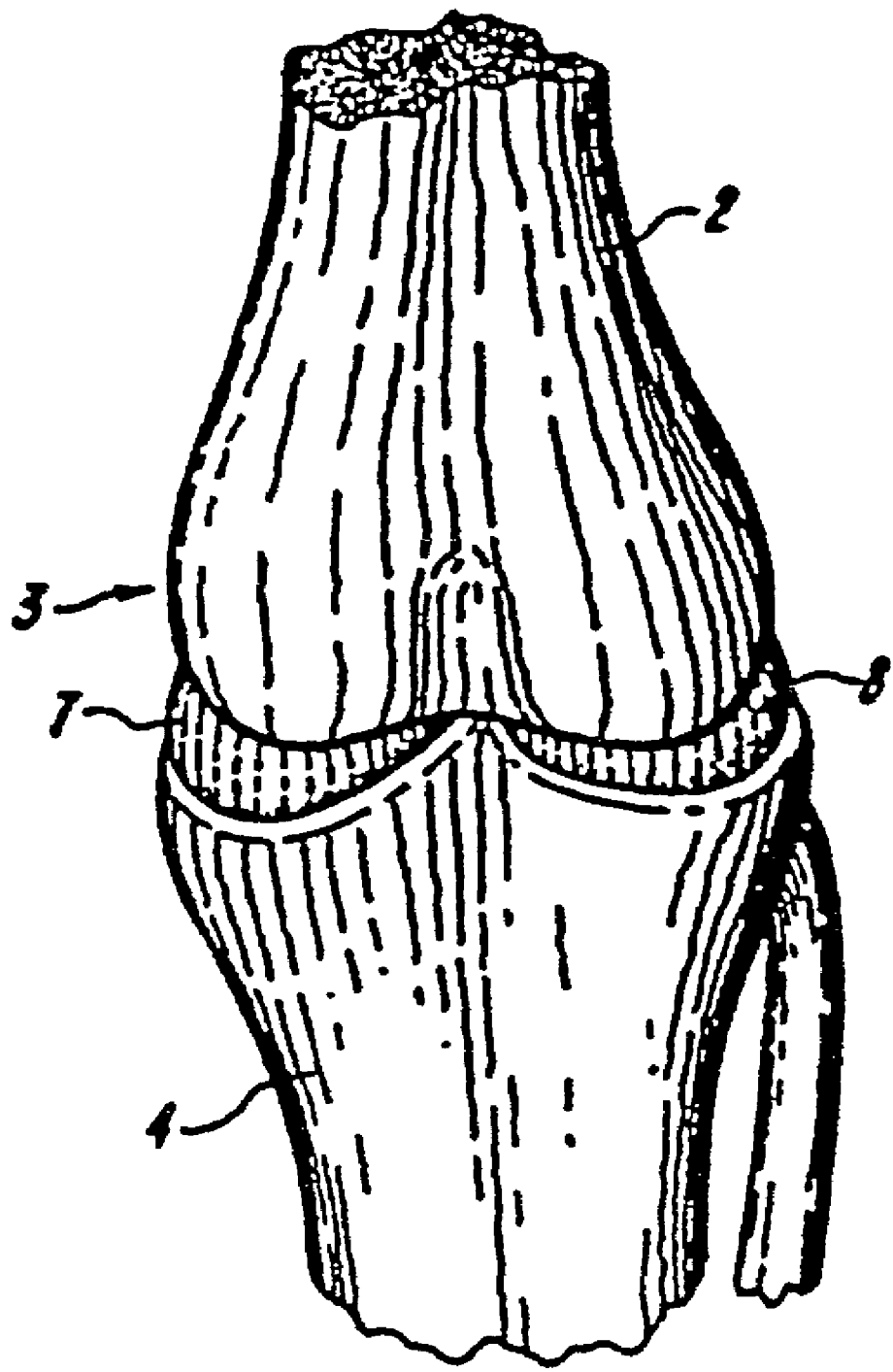
FIG. 1 is a simplified diagram of a human knee joint, with menisci in native positioning.
Figure 1A:
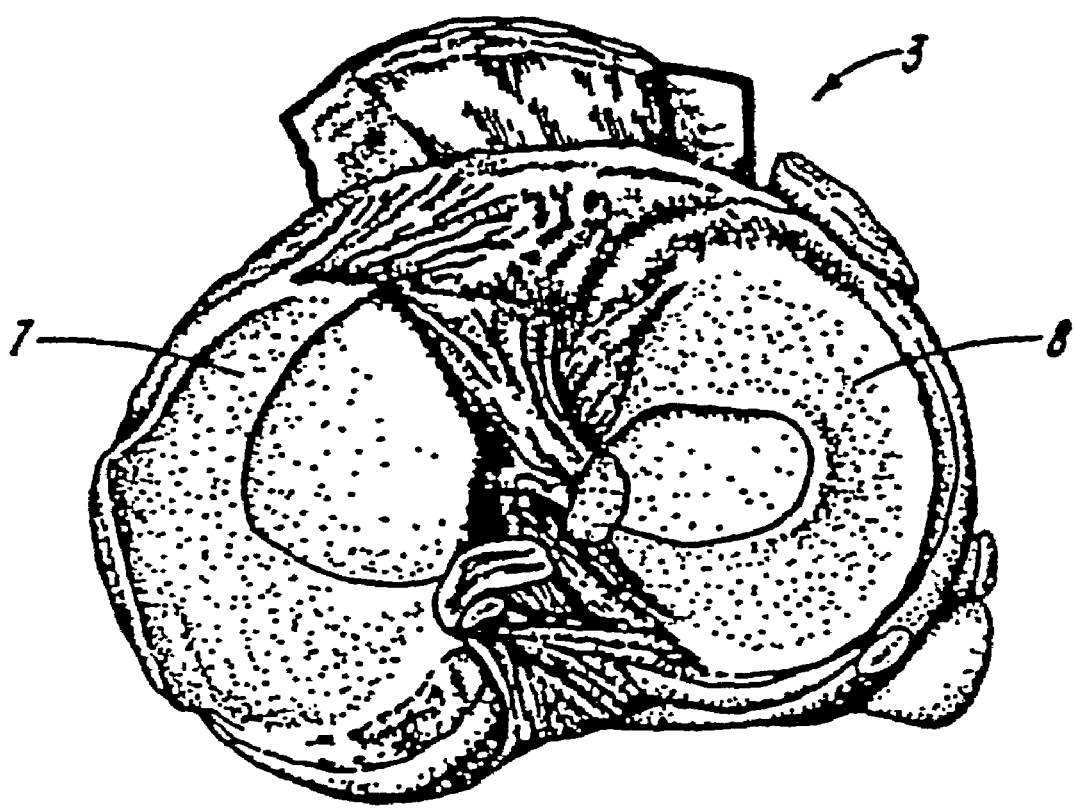
FIG. 1A is a diagram of a cut-away view of the knee joint showing the medial and lateral menisci as they are positioned in vivo over the medial and lateral condyles.

FIG. 1 is a diagram of the normal positioning of medial meniscus 7 and lateral meniscus 8 in the human knee joint 3 between the femur 2 and tibia 4. These menisci, when compressed between the femur 2 and tibia 4, become tough except at their points of attachment. FIG. 1A shows the in vivo structure of medial meniscus 7 and lateral meniscus 8 in the knee joint 3. The menisci conform to the shapes of the surfaces between which they are positioned, thereby resulting in two distinct in vivo forms. For example, the medial meniscus 7 has a relatively open crescent shape, while the lateral meniscus 8 has a relatively closed crescent shape.

Figure 2:
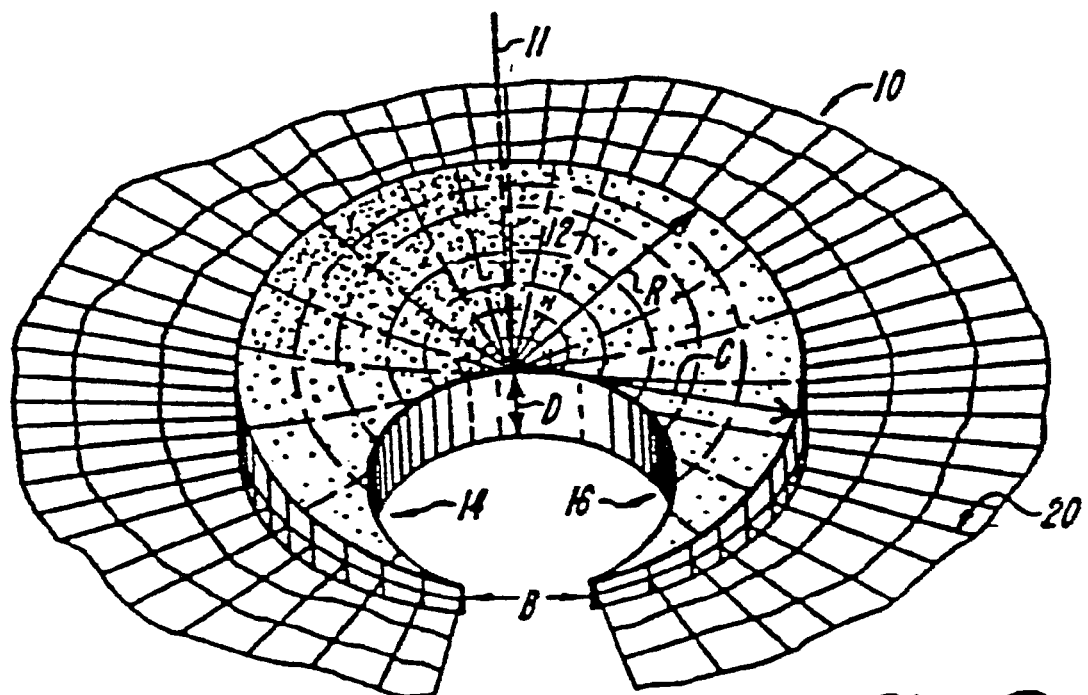
FIG. 2 shows a perspective view of an exemplary prosthetic meniscus in accordance with the invention.

An exemplary prosthetic meniscus 10 is shown in FIG. 2. The prosthetic meniscus 10 is a generally wedge-shaped, porous dry matrix or scaffold which extends circumferentially or laterally at least in part about a central axis 11. In the preferred form, the prosthetic meniscus 10 has the shape of a crescent-shaped wedge, extending circumferentially about the axis 11, and comprising a relatively wide central region 12 between two narrow distal regions 14 and 16. In the preferred form, the wedge has maximum height A at its peripheral edge of approximately 0.4 inches, a height D at its central point of approximately 0.2 inches, and a maximum radial dimension C of approximately 1.0 inches. The crescent shaped wedge subtends an angle B about axis 11 substantially in the range of about 135 to about 155 degrees, and preferably of about 150 degrees.

In the embodiment illustrated in FIG. 2, the prosthetic meniscus 10 includes a mesh member 20 extending from its peripheral edge. The mesh member 20 is composed of a biocompatible, bioresorbable material, and provides a readily used structure for anchoring the array 10 in place. The mesh member 20 may function in this capacity until sufficient tissue ingrowth occurs to then provide that function. By way of an example, the mesh member 20 may be a #1 mesh screen composed of absorbable suture materials such as polyglyconate, Dexon, or polydioxane (PDS) woven into a mesh. Non-absorbable suture materials such as Goretex® may also be used.

Figure 4:
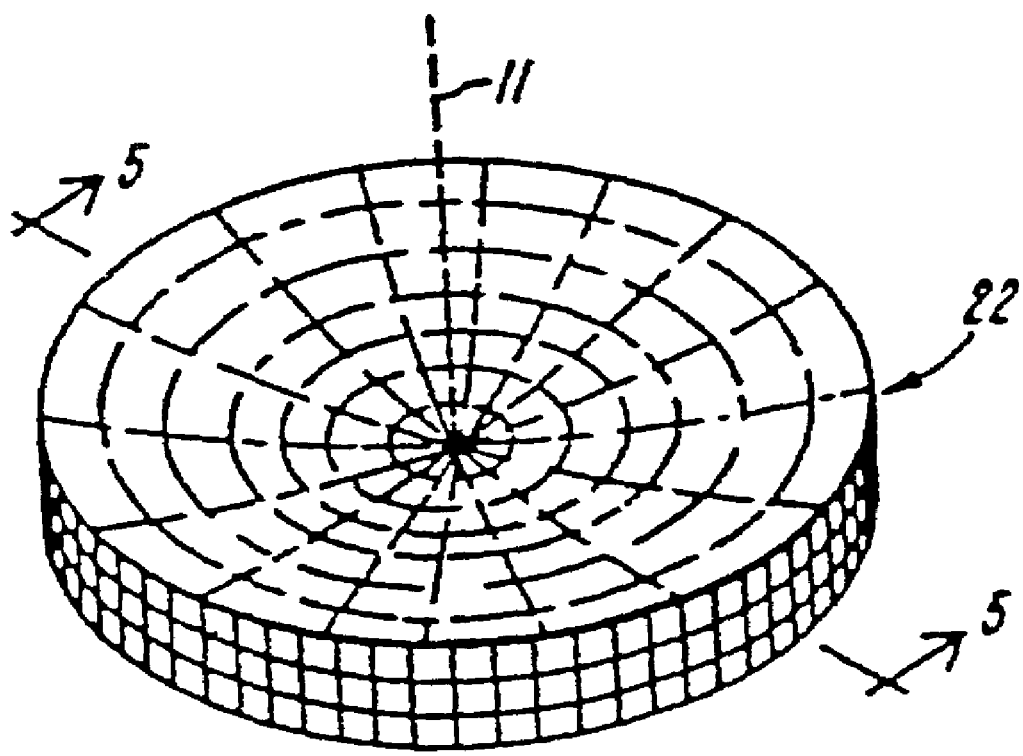
FIG. 4 shows a perspective view of an alternative embodiment of the invention.
Figure 5:
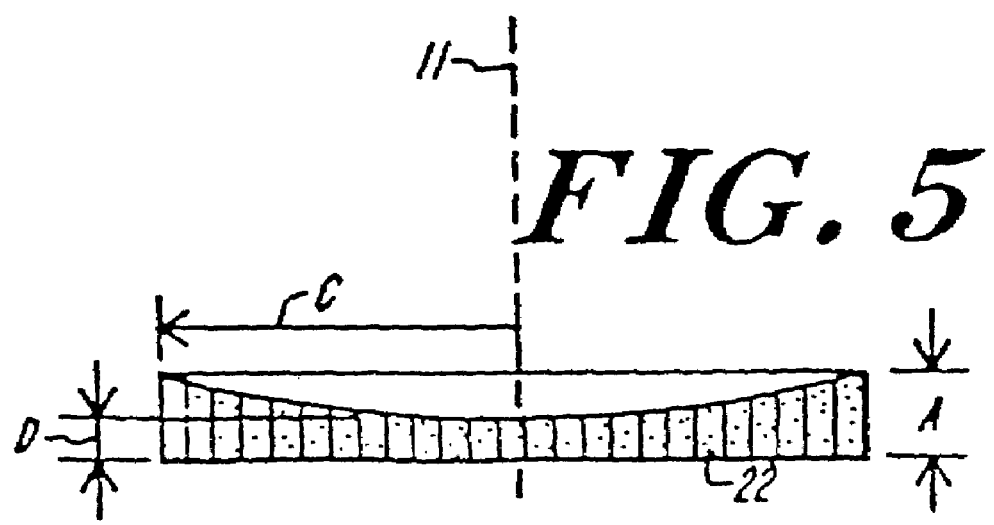
FIG. 5 shows a sectional view along line 5-5 of the prosthetic meniscus of FIG. 4.

FIGS. 4 and 5 show an additional embodiment of the invention, which is similar in composition to the prosthetic meniscus depicted in FIG. 2. More particularly, FIG. 4 depicts a right circular cylinder-shaped meniscus 22, extending fully about axis 11, i.e. where angle B equals 0 degrees (i.e. the meniscus subtends 360 degrees.) FIG. 5 shows a sectional view along line 5-5 of the meniscus shown in FIG. 4. The device illustrated in FIGS. 4 and 5 show the shape of the meniscus 22 when implanted; that is, the height D at areas 11 is less than the peripheral height A of the device. Prior to implantation, the device 22 may in some cases not have this relationship but upon implantation, the normal loads applied by the body force this conformation.

Definitions. The term "soft tissue", as used herein, refers to cartilaginous structures, such as meniscus and articular cartilage; and ligaments, such as anterior cruciate ligaments; and tendons. The term "xenograft" is synonymous with the term "heterograft" and refers to a graft transferred from an animal of one species to one of another species. *Stedman's Medical Dictionary* (Williams & Wilkins, Baltimore, Md., 1995). The term "xenogeneic", as in, for example, xenogeneic soft tissue refers to soft tissue transferred from an animal of one species to one of another species. Id.

The term "cellular disruption" as in, for example, cellular disruption treatment refers to a treatment for killing cells.

The term "portion" of a body part refers to all or less than all of the respective body part.

Once implanted in an individual, a xenograft can, if not treated, such as by the method of the invention, provoke immunogenic reactions such as chronic and hyperacute rejection of the xenograft. As used herein, the term "chronic rejection" refers to an immunological reaction in an individual against a xenograft being implanted into the individual. Typically, chronic rejection is mediated by the interaction of IgG natural antibodies in the serum of the individual receiving the xenograft and carbohydrate moieties expressed on cells, and/or cellular matrices and/or extracellular components of the xenograft. For example, transplantation of cartilage xenografts from non-primate mammals (e.g., porcine or bovine origin) into humans is primarily prevented by the interaction between the IgG natural anti-Gal antibody present in the serum of humans with the carbohydrate structure Galα1-3Galβ1-4G1cNAc-R (α-galactosyl or α-gal epitope) expressed in the xenograft. K. R. Stone et al., *Transplantation* 63: 640-645 (1997); U. Galili et al., *Transplantation* 63: (646-651 (1997). In chronic rejection, the immune system typically responds within one to two weeks of implantation of the xenograft. In contrast with "chronic rejection", "hyperacute rejection" as used herein, refers to the immunological reaction in an individual against a xenograft being implanted into the individual, where the rejection is typically mediated by the interaction of IgM natural antibodies in the serum of the individual receiving the xenograft and carbohydrate moieties expressed on cells. This interaction activates the complement system, causing lysis of the vascular bed and stoppage of blood flow in the receiving individual within minutes to two to three hours.

As used herein, the term "extracellular components" refers to any extracellular water, collagen and elastic fibers, proteoglycans, fibronectin, elastin, and other glycoproteins.

As used herein, the term "segmental meniscal defect" encompasses a tear or lesion (including radial tears, horizontal tears, bucket handle tears, complex tears) in less than the entire meniscus, resulting in partial resection of the meniscus. The meniscal augmentation device is composed of biocompatible and at least partially bioresorbable fibers, such as natural polymers, and typically has an outer surface contour substantially complementary to the segmental defect of the meniscus.

As used herein, the term "subject" includes living organisms susceptible to meniscal defects, e.g., mammals. Examples of subjects include humans, dogs, cats, horses, cows, goats, rats and mice.

As used herein, the term "cellular disruption" as in, for example, cellular disruption treatment, refers to a treatment for killing cells.

As used herein, the term "capping molecule", refers to a molecule that links with carbohydrate chains such that the xenograft is no longer recognized as foreign by the subject's immune system.

As used herein, the terms "to cap" or "capping", refer to linking a capping molecule such as a carbohydrate unit to the end of a carbohydrate chain, as in, for example, covalently linking a carbohydrate unit to surface carbohydrate moieties on the xenograft.

As used herein, the term "first surface carbohydrate moiety (moieties)" refers to a terminal α-galactosyl sugar at the non-reducing end of a carbohydrate chain.

As used herein, the term "second surface carbohydrate moiety (moieties)" refers to a N-acetyllactosamine residue at the non-reducing end of a carbohydrate chain, the residue being non-capped either naturally or as a result of prior cleavage of an α-galactosyl epitope.

Substantially Immunologically-Compatible Matrix Material. In the first step of the method of the invention, an intact soft tissue is removed from a non-human animal. Medial or lateral meniscus is removed from the knee joints of the non-human animal. Articular cartilage is removed from any joint of the non-human animal. Ligaments and tendons, such as, for example, the Achilles tendon, are also removed from non-human animals.

The joint which serves as the source of the soft tissue should be collected from freshly killed animals and preferably immediately placed in a suitable sterile isotonic or other tissue preserving solution. Harvesting of the joints should occur as soon as possible after slaughter of the animal and preferably should be performed in the cold, i.e., in the approximate range of about 5° C. to about 20° C., to minimize enzymatic degradation of the soft tissue. Preferably, the soft tissue is harvested in the cold, under strict sterile technique.

With respect to meniscal soft tissue, the joint is opened by first transecting the patellar tendon. The horns of the menisci are dissected free of adhering tissue. A small amount of bone representing a substantially cylindrical plug of approximately five millimeters in diameter by five millimeters in depth may be left attached to the horns. The meniscal synovial junction is carefully identified and freed from the meniscus tissue itself, thereby forming the matrix material.

With respect to articular cartilage soft tissue, a fine peel of articular cartilage with a small layer of subchondral bone is shaved from the donor joint to form the matrix material.

With respect to ligament soft tissue, the donor joint is opened by standard surgical technique. Preferably, the ligament is harvested with a block of bone attached to one or both ends, although in some forms of the invention the ligament alone is harvested. In one form of the invention, a block of bone representing a substantially cylindrical plug of approximately 9-10 mm in diameter by approximately 20-40 mm in length may be left attached to the ligament. The ligament is carefully identified and dissected free of adhering tissue, thereby forming the matrix material.

With respect to heart valve soft tissue, porcine peritoneum or pericardium is harvested to form the matrix material according to procedures known to those of ordinary skill in the art. See, for example, the peritoneum harvesting procedure discussed in U.S. Pat. No. 4,755,593 by Lauren.

The resulting matrix material is then washed in about ten volumes of sterile cold water to remove residual blood proteins and water-soluble materials. The matrix material is then immersed in alcohol at room temperature for about five minutes, to sterilize the tissue and to remove non-collagenous materials.

The matrix material is subjected to a cellular disruption treatment to kill the cells of the soft tissue. Typically after surface carbohydrate moieties have been removed from living cells and the extracellular components, the living cells re-express the surface carbohydrate moieties. Re-expression of antigenic moieties of a matrix material can provoke continued immunogenic rejection of the matrix material. In contrast, dead cells are unable to re-express surface carbohydrate moieties. Removal of antigenic surface carbohydrate moieties from dead cells and the extracellular components of a matrix material substantially and permanently eliminates antigenic surface carbohydrate moieties as a source of immunogenic rejection of the prosthetic meniscus.

Accordingly, in the above-identified embodiments, the matrix material is subjected to freeze/thaw cycling as discussed above to disrupt, i.e., to kill the cells of the soft tissue. Alternatively, the matrix material of the device of the invention is treated with gamma radiation having an amount of 0.2 MegaRad up to about 3 MegaRad. Such radiation kills the soft tissue cells and sterilizes the matrix material. Once killed, the soft tissue cells are no longer able to re-express antigenic surface carbohydrate moieties, such as α-gal epitopes, which are factors in the immunogenic rejection of transplanted xenografts.

Either before or after the soft tissue cells are killed, in embodiments of the invention, the matrix material is subjected to in vitro digestion of the matrix material with glycosidases, and specifically galactosidases, such as α-galactosidase, to enzymatically eliminate antigenic surface carbohydrate moieties. In particular, α-gal epitopes are eliminated by enzymatic treatment with α-galactosidases, as shown in the following reaction:

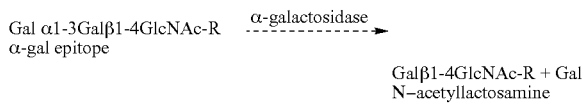

The N-acetyllactosamine residues are epitopes that are normally expressed on human and mammalian cells and thus are not immunogenic. The in vitro digestion of the matrix material with glycosidases is accomplished by various methods. For example, the matrix material can be soaked or incubated in a buffer solution containing glycosidase. Alternatively, a buffer solution containing the glycosidase can be forced under pressure into the matrix material via a pulsatile lavage process.

Elimination of the α-gal epitopes from the matrix material diminishes the immune response against the matrix material. The α-gal epitope is expressed in non-primate mammals and in New World monkeys (monkeys of South America) as $1\times10^6$–$35\times10^6$ epitopes per cell, as well as on macromolecules such as proteoglycans of the extracellular components. U. Galili et al., *J. Biol. Chem.* 263: 17755 (1988). This epitope is absent in Old World primates (monkeys of Asia and Africa and apes) and humans, however. Id. Anti-Gal is produced in humans and primates as a result of an immune response to α-gal epitope carbohydrate structures on gastrointestinal bacteria. U. Galili et al., *Infect. Immunol.* 56: 1730 (1988); R. M. Hamadeh et al., *J. Clin. Invest.* 89: 1223 (1992). Since non-primate mammals produce α-gal epitopes, xenotransplantation of xenografts from these mammals into primates results in rejection because of primate anti-Gal binding to these epitopes on the xenograft. The binding results in the destruction of the xenograft by complement fixation and by antibody dependent cell cytotoxicity. U. Galili et al., *Immunology Today* 14: 480 (1993); M. Sandrin et al., *Proc. Natl. Acad. Sci. USA* 90: 11391 (1993); H. Good et al., *Transplant. Proc.* 24: 559 (1992); B. H. Collins et al., *J. Immunol.* 154: 5500 (1995). Furthermore, xenotransplantation results in major activation of the immune system to produce increased amounts of high affinity anti-Gal. Accordingly, the substantial elimination of α-gal epitopes from cells and from extracellular components of the xenograft, and the prevention of re-expression of cellular α-gal epitopes can diminish the immune response against the prosthetic device associated with anti-Gal antibody binding with α-gal epitopes.

Further, the prosthetic devices of the invention are particularly well suited to in vitro enzymatic elimination of the α-gal epitopes. In contrast to organs and other tissues, the cartilage extracellular components undergo extremely slow turnover. Moreover, once the cartilage cells, i.e., the fibrochondrocytes are killed, these cells are prevented from re-expressing the α-gal epitopes, as discussed above.

In addition, the soft tissue matrix material may be treated with polyethylene glycol (PEG) prior to or concurrently with treatment with glycosidase. PEG acts as a carrier for the glycosidase by covalently bonding to the enzyme and to the collagen extracellular components. Further, PEG-treated xenografts have reduced immunogenicity.

Either before or after the soft tissue cells are killed, in embodiments of the invention, the matrix material is washed or digested with one or more different types of proteoglycan-depleting factors. The proteoglycan-depleting factor treatment can precede or follow glycosidase treatment. Proteoglycans such as glycosaminoglycans (GAGs) are interspersed either uniformly as individual molecules or within varying amounts within the extracellular components of the matrix material. The GAGs include mucopolysaccharide molecules such as chondroitin 4-sulfate, chondroitin 6-sulfate, keratan sulfate, dermatan sulfate, heparin sulfate, hyaluronic acid, and mixtures thereof. The proteoglycans including such GAGs contain attached carbohydrates such as α-gal epitopes. Such epitopes stimulate an immune response once the xenograft is transplanted, as discussed above. Washing or digesting the matrix material with the proteoglycan-depleting factor removes at least a portion of the proteoglycans and attached α-gal epitopes from the extracellular components of the matrix material, and thereby diminishes the immune response against the prosthetic device upon its transplantation. After the proteoglycan-depleting factor treatment and subsequent transplantation, natural tissue can repopulate the remaining collagen shell.

Non-limiting examples of the proteoglycan-depleting factors used in the method of the invention include proteoglycan-depleting factors such as chondroitinase ABC, hyaluronidase, chondroitin AC II lyase, keratanase, and trypsin. Other proteoglycan-depleting factors used in the method of the invention include fragments of fibronectin. Homanberg et al. suggest that fibronectin fragments, such as the amino-terminal 29-kDa fragment, bind to the superficial surface of articular cartilage soft tissue and penetrate the cartilage to surround the cartilage cells. G. A. Homandberg et al., *Biochem. J.* 321: 751-757 (1997); G. A. Homandberg et al., *Osteoarthritis and Cartilage* 5: 309-319 (1997); G. A. Homandberg et al., *Archives Of Biochemistry And Biophysics* 311(2): 213-218 (June 1994); G. A. Homandberg et al., *Inflammation Research* 46: 467-471 (1997). At selected concentrations, Homanberg et al. further suggest that the addition of such fibronectin fragments to cartilage in vitro or in vivo results in the temporary suppression of proteoglycan synthesis and the enhancement of extracellular metalloproteinases which in turn cause a rapid proteoglycan loss from cartilage tissue. Id.

Other proteoglycan-depleting factors known to those of ordinary skill in the art are also possible for use with the invention, however. The matrix material of the device is treated with proteoglycan-depleting factor in an amount effective for removing at least a portion of the proteoglycans from the extracellular components of the matrix material. Preferably, the matrix material is treated with proteoglycan-depleting factor such as hyaluronidase in an amount ranging from about 1.0 TRU/ml to about 100.0 TRU/ml or proteoglycan-depleting factor such as chondroitinase ABC in an amount ranging from about 0.01 u/ml to about 2.0 u/ml or most preferably, in an amount ranging from about 1.0 μl/ml to about 2.0 μ/ml. The matrix material can also be treated with proteoglycan-depleting factor such as fibronectin fragment, (e.g., amino terminal 29-kDa fibronectin fragment) in an amount ranging from about 0.01 μM to about 1.0 μM, and preferably in an amount ranging from about 0.1 μM to about 1.0 μM.

Following treatment with glycosidase or treatment with proteoglycan-depleting factors, the remaining carbohydrate chains (e.g., glycosanlinoglycans) of the matrix material are optionally treated with capping molecules to cap at least a portion of the remaining carbohydrate chains. Examples of capping molecules used in the method of the invention include fucosyl and N-acetyl glucosamine.

Construction of the Prosthetic Device. The fibers of the meniscal augmentation device of the invention can be prepared from the substantially immunologically-compatible matrix material described above, where the matrix material is in the form of a dry, porous volume matrix, a portion of which may be cross-linked. In a preferred embodiment, the matrix material can be chosen for the ability to provide lubrication as well as mechanical strength.

The porous matrix of the prosthetic device encourages ingrowth of meniscal fibrochondrocytes, endothelial cells, fibroblasts, and other cells that normally occupy the extracellular matrix as well as synthesize and deposit extracellular matrix components. These fibers include collagen, elastin, reticulin, analogs thereof and mixtures thereof, which are generally obtained from animal tissue and made with reduced immunogenicity as described above. In some forms of the invention, the fibers may be randomly oriented throughout the matrix. Alternatively, the fibers may assume substantially circumferentially extending or substantially radially extending orientation throughout the meniscal augmentation device. The density of the fibers of the meniscal augmentation device may be uniform or non-uniform throughout the device. In the non-uniform configuration, relatively high densities of fibers may be established at anticipated points of high stress.

The device can also be constructed of other biopolyers, such as cellulose, alginic acid, chitosan, and analogs thereof, and mixtures thereof (in addition to or conjunction with collagen, elastin, and reticulin).

To encourage ingrowth of meniscal fibrochondrocytes (including vertebral fibrochondrocytes or articular fibrochondrocytes) and other types of cells into the porous volume matrix, while at the same time preserving the mechanical strength and cushioning ability of the device, the density of the meniscal augmentation device can be manipulated. For example, if a relatively great intrafibrillary and interfibrillary space is desired to encourage tissue growth into the matrix, the density of the device can be in the range from about 0.07 to about 0.15 g matrix/cm$^3$, where g/cm$^3$ represents the number of grams in a cubic centimeter of the matrix.

Alternatively, the density can be about 0.07 to 0.50 g matrix/cm$^3$, or more particularly, about 0.10 to about 0.25 g matrix/cm$^3$.

Alternatively, if a relatively small intrafibrillary and interfibrillary space is desired to provide mechanical support for the knee joint and improved cushioning, the density of the device be designed to be in the range from about 0.15 to about 0.50 g matrix/cm$^3$. In a preferred embodiment, the matrix has a density of about 0.10 to about 0.25 g matrix/cm$^3$ with an intrafibrillary and interfibrillary space of about 8 cm$^3$/g matrix to about 9 cm$^3$/g matrix, which offers an ideal environment for ingrowth of meniscal fibrochondrocytes as well as other cells while maintaining sufficient mechanical strength to support natural meniscal load forces.

Alternatively, the device matrix can have an intrafibrillary and interfibrillary space of about 2 to 25 cm$^3$/g matrix material, or 2 to 14 cm$^3$/g matrix.

In one embodiment, the prosthetic device is a prosthetic intervertebral disc, the matrix being adapted to have in vivo an outer surface contour substantially the same as that of a natural intervertebral disc. The device matrix thus establishes an at least partially bioresorbable scaffold adapted for ingrowth of vertebral fibrochondrocytes and the device matrix and the ingrown vertebral fibrochondrocytes support natural intervertebral load forces. The device is in the shape of a disc, and the fibers in the device matrix can be oriented in a substantially ordered fashion in the region adjacent to the peripheral edge of the disc, the orientation being substantially circumferential. In one particular embodiment, the matrix material includes low density filaments having a density of about 0.05 to about 0.40 g/cm$^3$. In another particular embodiment, the low density filaments are from about 0.07 to about 0.30 g/cm$^3$.

In another embodiment, the prosthetic device is a prosthetic ligament, with the matrix material being made of a plurality of substantially aligned, elongated filaments. The filaments of the device matrix establish a bioresorbable scaffold adapted for ingrowth of ligament fibroblasts, and the device matrix and the ingrown fibroblasts support natural ligament tensile forces.

In a particular embodiment, the device matrix material includes fibrils (such as protein fibrils) that are present in the matrix at a concentration of about 75 to 100% by dry weight, and polysaccharide molecules (such as glycosaminoglycans) that are present at a concentration of about 0 to 25% by dry weight.

Cross-linking. The matrix can also include glycosaminoglycan molecules (GAGs) interspersed throughout the fibers. These molecules contain chains of repeating disaccharide units containing an N-acetylated hexosamine and provide lubrication and cross-links for the meniscal augmentation device. Examples of GAGs that can be used in the method of the invention include chondroitin 4-sulfate, chondroitin 6-sulfate, keratan sulfate, dermatan sulfate, heparan sulfate, hyaluronic acid, and mixtures thereof as components of the matrix. The GAGs can be uniformly dispersed throughout the meniscal augmentation device as individual molecules, or they can be present in varying amounts in different regions of the device. The matrix can be composed of about 75-100% natural fibers and about 0-25% GAGs by dry weight. These proportions can be constant or variable throughout the matrix.

In one embodiment, the device matrix material includes collagen and glycosaminoglycan cross-links. The glycosaminoglycan cross-links are present at a density less than about 0.95 and greater than about 0.50 cross-link/collagen ratio.

In another embodiment, the molecular weight of the molecular cross-links is within the range of about 800-60,000 daltons.

The temporary stability of the shape of the meniscal augmentation device when in vivo, and the rate of resorption of the fibers (and GAGs if the device contains GAGs), are both attributed to cross-links between at least a portion of the fibers. In addition, GAGs can directly participate in the formation of covalent cross-links with the fibers or can interact mechanically with the fibers by entanglement to form stable fiber-GAG complexes. The cross-linking reagents used to form these cross-links include biocompatible bifunctional reagents. These reagents can interact with amino, carboxyl, or hydroxyl groups on a single molecule to form intramolecular cross-links. Alternatively, they may interact with amino, carboxyl, or hydroxyl on different molecules or on fibers and GAGs to form intermolecular cross-links. Useful cross-linking reagents include glutaraldehyde, formaldehyde, biocompatible bifunctional aldehydes, carbodiimides, hexamethylene diisocyanate, bis-ionidates, polyglycerol polyglycidyl ether, glyoxal, bisimidates, adipyl chloride and mixtures thereof.

Intermolecular cross-links can also be established through a dehydrothermal process (heat and vacuum), which results in peptide bond formation between an amino group of lysine or hydroxylysine and a carboxyl group of aspartic acid or glutamic acid. The cross-linked device has a relatively high thermal stability between about 55° C. to 85° C., preferably between 65° C. to 75° C., for sufficient in vivo stability. This may be achieved through manipulation of the cross-linking conditions, including reagent concentration, temperature, pH, and time.

The cross-linked device maintains a sufficient degree of hydrophilicity and elasticity, thereby simulating the properties of a natural meniscus or a portion thereof (i.e., the ability to sustain mechanical stress and to protect and lubricate articular surfaces). In addition the structure provides an ideal environment for cell infiltration and extracellular matrix synthesis and deposition.

The invention further pertains to a method of fabricating a meniscal augmentation device. The method generally includes placing a plurality of fibers (or fibers and GAGs, or fibers and growth factors and/or adhesion factors and/or GAGS), into a mold having a shape defined by the segmental defect in the meniscus which is to be repaired (or defining a shape larger than that of the segmental defect to be repaired), lyophilizing the fibers, and contacting the fibers or the fibers and GAGs with a chemical cross-linking reagent such that the fibers or the fibers and GAGs assume the shape of the mold to obtain a dry, porous volume matrix. The mold may define the outer surface of the device to complement the segmental defect. Alternatively, in cases where the other aspects of the invention, an additional cross-linking step is performed by lyophilizing the chemically cross-linked matrix and then subjecting it to dehydrothermal cross-linking procedures. In cases where the mold defines a shape larger than a specific defect-to-be-repaired, the outer contour of the matrix may be cut so that it complements the defect.

A mold 100 useful for fabricating the prosthetic meniscus is made of implantable stainless steel or biocompatible plastics such as Teflon®, polypropylene, Delrin®, or combination of these materials. The mold 100 is composed of three pieces 102, 104, and 106 as shown in FIGS. 6-8.

Figure 6:
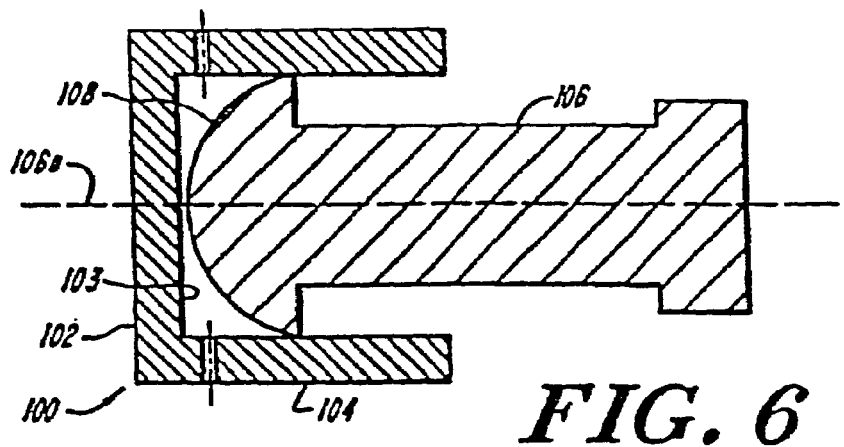
FIG. 6 shows a mold designed for the fabrication of a prosthetic meniscus having a cylindrical pad shape.

By way of example for the disk-shaped meniscus illustrated in FIGS. 4 and 5, the mold 100 of FIG. 6 is used. The first piece 102 is disk-like and has a diameter substantially equal to that of the desired meniscus. Piece 102 is perforated to allow liquid to pass through under pressure. The inner surface 103 of piece 102 has the desired shape of one side of the meniscus-to-be-formed.

The second piece 104 is a hollow cylinder that has the same inner dimension as the first piece 102. The third piece 106 is a cylindrical piston that has an outer diameter slightly less than the inner diameter of piece 104. The "top", or crown, surface 108 of piston 106 has the desired shape of one side of the meniscus-to-be-formed.

Figure 3:
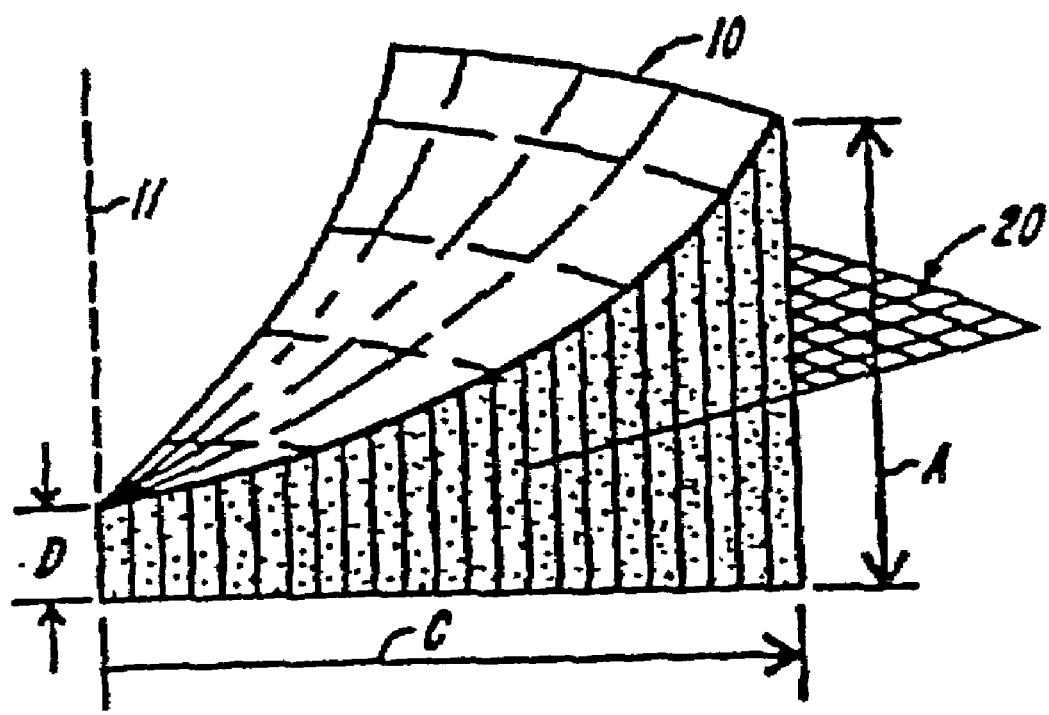
FIG. 3 shows a perspective radial section of the prosthetic meniscus of FIG. 2.
Figure 7:
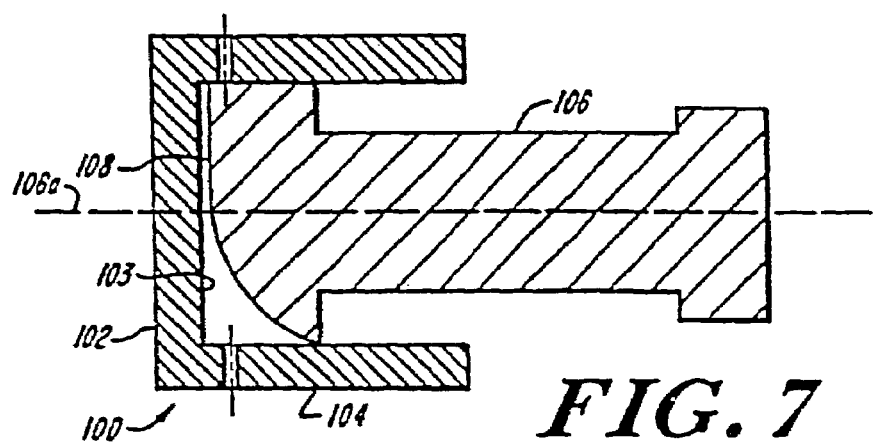
FIG. 7 shows a mold designed for the fabrication of a prosthetic meniscus having a crescent-shaped wedge form.
Figure 8:
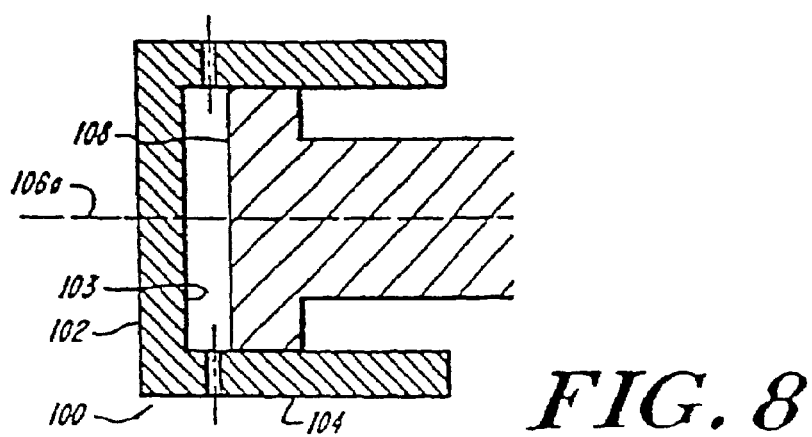
FIG. 8 shows a mold designed for the fabrication of a cylindrical prosthetic meniscus.

For the meniscus of FIG. 3, the mold of FIG. 7 is used where the shape of piece 102, and cross-section of piece 104 have the shape of an angular segment. For a flat circular disk meniscus, the mold 100 of FIG. 8 is used where pieces 102 and 104 are the same as in FIG. 6 and piece 106 is similar to that piece in FIG. 108 but has a flat crown surface 108.

During fabrication of the meniscus 10, the piece 102 is first assembled within piece 104, as shown in FIGS. 6-8. The constituent fibers (in a fluid) are placed against the surface 103 of piece 102. Then the crown surface 108 of piston 106 is driven toward surface 103 along a compression axis 106a until the fibers are compressed, the fluid is driven out through piece 102, and the desired axial dimension of the compressed fiber array is attained. The mold is then frozen in preparation for chemical cross-linking.

In one embodiment, the fibers of the matrix material are oriented in a substantially random fashion throughout the matrix. In other embodiments, the fibers of the matrix material are oriented in a substantially ordered fashion throughout the matrix. For example, the fibers can be substantially circumferentially extending fibers or substantially radially extending fibers. Moreover, the density of the fibers of the matrix material can be substantially uniform throughout the matrix or dispersed non-uniformly throughout the matrix.

Accordingly, the fibers are placed randomly or oriented in specific directions in, for example, mold forms such as a cylindrical form. For example, the fibers of the matrix material can be placed in the mold in a circumferential orientation by rotating the mold as the fibers are placed therein. Alternatively, the fibers can be oriented radially in the mold by manually painting the fibers in a linear, radially directed pattern. Other components such as GAGs which may participate in the cross-linking reactions, can be mixed in with the fibers in a random or non-random fashion before the structure is subjected to various cross-linking and dehydrating procedures including various chemical and/or dehydrothermal methods. Adhesion molecules or adhesive fragments or analogs thereof, or growth factors or biologically active fragments or analogs thereof, may be incorporated into this structure during processing.

In another embodiment of using the mold to fabricate the device, the fabricating includes the steps of (1) placing a plurality of biocompatible glycosidase-treated fibers into a mold; (2) subjecting the fibers to a first and a second cycle of freezing and thawing; (3) contacting the fibers with a chemical cross-linking agent such that the fibers assume the shape of the mold; and (4) lyophilizing the cross-linked fibers. Alternatively, the fabricating of the device can include the steps of orienting glycosidase-treated fibers of the matrix material substantially circumferentially by compressing the fibers in the mold with a piston, wherein the piston motion is substantially directed along a compression axis, while during the compressing step the piston is rotated with respect to the mold about the compression axis.

Specific densities and pore sizes can be obtained in various regions of the matrix by compressing the fibers or the fibers and GAGs in the mold prior to the chemical cross-linking step. This may be accomplished by applying pressure to a specific region of the matrix with a piston of a predetermined shape. A preferred pore size range is from about 50 microns to about 500 microns. Alternatively, the pore size can be substantially in the range 10-50 microns.

By following the processes described in the above examples, a meniscal augmentation device of the invention can be constructed having the characteristics listed below in TABLE I.

TABLE I

| Physical Characteristics | |
|---|---|
| Inner margin height | 2-10 mm |
| Outer margin height | 4-10 mm |
| density | 0.07-0.05 g/cm$^2$ |
| intra- and interfibrillary space | 3.5-9.5 cm$^3$/g matrix |
| Constituents | |
| fiber (collagen) content | 75-100% |
| GAG content | 0-25% |
| growth factors | 0-1% |
| adhesion molecules | 0-1% |

Furthermore, when an aldehyde such as, for example, glutaraldehyde is used as the cross-linking agent, the matrix material may be placed in a buffered solution containing about 0.001% to about 5.0% glutaraldehyde and preferably, about 0.01% to about 5.0% glutaraldehyde, and having a pH of about 7.4. More preferably about 0.01% to about 0.10% aldehyde, and most preferably about 0.01% to about 0.05% aldehyde is used. Any suitable buffer may be used, such as phosphate buffered saline or trishydroxymethylaminomethane, and the like, so long as it is possible to maintain control over the pH of the solution for the duration of the cross-linking reaction, which may be from one to fourteen days, and preferably from one to five days, and most preferably from three to five days.

Alternatively, the matrix material can be exposed to a cross-linking agent in a vapor form, including, but not limited to, a vaporized aldehyde cross-linking agent, such as, for example, vaporized formaldehyde. The vaporized cross-linking agent can have a concentration and a pH and the matrix material can be exposed to the vaporized cross-linking agent for a period of time suitable to permit the cross-linking reaction to occur. For example, the matrix material can be exposed to vaporized cross-linking agent having a concentration of about 0.001% to about 5.0% and preferably, about 0.01% to about 5.0%, and a pH of about 7.4. More preferably, the matrix material is exposed to the aldehyde in an amount ranging from about 0.01% to about 0.10%, and most preferably to an aldehyde ranging in an amount from about 0.01% to about 0.05%. The matrix material is exposed to the aldehyde for a period of time which can be from one to fourteen days, and preferably from one to five days, and most preferably from three to five days. Exposure to vaporized cross-linking agent can result in reduced residual chemicals in the matrix material from the cross-linking agent exposure.

The cross-linking reaction should continue until the immunogenic determinants are substantially eliminated from the matrix material, but the reaction should be terminated prior to significant alterations of the mechanical properties of the matrix material. When diamines are also used as cross-linking agents, the glutaraldehyde cross-linking should occur after the diamine cross-linking, so that any unreacted diamines are capped. After the cross-linking reactions have proceeded to completion as described above, the matrix material should be rinsed to remove residual chemicals, and 0.01-0.10 M glycine, and preferably, 0.01-0.05 M glycine may be added to cap any unreacted aldehyde groups which remain.

In another embodiment, the prosthetic device may be constructed mainly of Type I collagen fibers, prepared as described above (by treatment with $\alpha$-galactosidase to eliminate $\alpha$-Gal epitopes), without GAG cross-links.

Moreover, different types of collagen, such as Type II collagen, or collagen obtained from other sources, such as biosynthetically-produced collagen or analogs thereof, can also be used in the construction of the meniscal augmentation device.

Additional Tissue Preparation Steps. In addition to the preparation of tissues described above (by treatment with $\alpha$-galactosidase to eliminate $\alpha$-Gal epitopes), the tissues can be treated with a series of mechanical and chemical methods to either totally remove the non-collagenous materials or reduce them to a minimal level. The tendon or skin can be mechanically disintegrated into fine pieces useful for further processing. The disintegration may be achieved by grinding the tissue at liquid nitrogen temperature, or by cutting the tissue into small pieces with a sharp knife. In certain applications, the tendons are mechanically disintegrated along the fiber direction in order to maintain the length of the fibers for mechanical strength.

Salt extraction of tendon at neutral pH removes a small portion of the collagen molecules that are newly synthesized and have not yet been incorporated into the stable fibrils. Salt also removes some glycoproteins and proteoglycans that are associated with collagen through electrostatic interactions. Other salts such as KCl and the like can be used as a substitute for NaCl.

Lipids that are associated with the cell membranes or collagenous matrices may be removed by first extracting with detergents such as Triton X-100, followed by extracting with ether-ethanol mixtures. The concentration of Triton X-100 is usually about 2-4%, but is preferably about 3%. The preferred mixture of ether-ethanol is usually at about a 1:1 ratio (v/v). The period of extraction is usually from 8 hours to 96 hours, preferably from about 24 to 48 hours.

Further extraction may be accomplished by matrix swelling conducted at two extreme pHs. Both acidic and basic swelling weakens the non-covalent intermolecular interactions, thus facilitating the release of non-covalently attached glycoproteins, GAGs, and other non-collagenous molecules through the open pores of the collagenous matrices.

The swelling of matrix at alkaline pH is done by treating the collagen at high pH with $Ca(OH)_2$, NaOH, or the like, for a period of about 8 to 96 hours. Alkali extraction in the presence of triple-helical stabilizing salts such as $(CH_3)_4NCl$, $(NH_4)_2SO_4$, or the like reduces the potential risk of denaturation of the collagen. Alkali treatment dissociates the non-cross-linked glycoproteins and GAGs from the collagen matrices. The alkali also removes the residual lipids through saponification.

The acid swelling may be conducted at a low pH in the presence of acetic acid, HCl, or the like. Like the alkali treatment, the acid swelling removes non-cross-linked glycoproteins and GAGs.

After alcohol immersion, the matrix material may be subjected to at least one of the following treatments: radiation treatment, treatment with alcohol, ozonation, one or more cycles of freezing and thawing, and/or treatment with a chemical cross-linking agent. When more than one of these treatments is applied to the matrix material, the treatments may occur in any order.

In one embodiment of the method of the invention, the matrix material may be treated by exposure to ultraviolet radiation for about fifteen minutes or gamma radiation in an amount of about 0.5 to 3 MegaRad.

In another embodiment, the matrix material may be treated by again being placed in an alcohol solution. Any alcohol solution may be used to perform this treatment. Preferably, the matrix material is placed in a 70% solution of isopropanol at room temperature.

In a further embodiment of the method of the invention, the matrix material may be treated by freeze/thaw cycling. For example, the matrix material may be frozen using any method of freezing, so long as the matrix material is completely frozen, i.e., no interior warm spots remain which contain unfrozen soft tissue. Preferably, the matrix material is dipped into liquid nitrogen for about five minutes to perform this step of the method. More preferably, the matrix material is frozen slowly by placing it in a freezer. In the next step of the freeze/thaw cycling treatment, the matrix material is thawed by immersion in an isotonic saline bath at room temperature (about 25° C.) for about ten minutes. No external heat or radiation source is used, in order to minimize fiber degradation.

In yet a further embodiment, the matrix material may optionally be exposed to a chemical agent to tan the proteins within the extracellular components, to further diminish or reduce the immunogenic determinants present in the matrix material, as described in detail in U.S. Pat. No. 4,755,593. Any tanning agent may be used for this treatment.

Adhesion Molecules, Growth Factors and Other Additions to the Matrix Material. The prosthetic meniscal augmentation device may further include an adhesion molecule, or adhesive portion or analog thereof, which is incorporated within the network of fibers. As used herein, an adhesion molecule is one that aids in meniscal tissue regeneration by providing a tacky surface in the device to which cells can stick. Useful adhesion molecules include, but are not limited to, chondronectin, osteonectin, and fibronectin (see e.g., U.S. Pat. Nos. 4,589,881, 4,661,111, and 4,578,079), a portion of which can be conjugated to, for example, chondroitin sulfate, and the like.

Alternatively, or in addition, the prosthetic augmentation device may include growth factors interspersed throughout and incorporated throughout the network of fibers, and which aid in meniscal tissue regeneration. The growth factors include, but are not limited to, transforming growth factor-$\alpha$, transforming growth factor-$\beta$, fibroblast growth factor, epidermal growth factor, platelet derived growth factor, and the like, and analogs of such growth factors having the biological activity of its corresponding natural growth factor. The matrix may also contain more than one type of growth factor in any combination.

Methods of Use. The invention further pertains to a method for regenerating meniscal tissue in vivo. This method includes fabricating a meniscal augmentation device by the method described above and implanting the meniscal augmentation device into a segmental defect in the meniscus of a subject.

The prosthetic device may be implanted into damaged human joints by those of skill in the art using known arthroscopic surgical techniques. Specific instruments for performing arthroscopic techniques are known to those of skill in the art, which ensure accurate and reproducible placement of soft tissue implants.

Once the prosthetic device is placed within a body, it aids in the proliferation of new blood vessels, which is important for the wound-healing process. The blood vessels nourish the graft and supply vital molecules that the body needs to rebuild the damaged tissue. The material also strengthens in response to stress, much like natural tissue.

Base Component. The prosthetic device may also include a biocompatible conical base component, including an anchor for anchoring the device in a complimentary aperture in cancellous bone. The base component extends from portions of the outer surface of the matrix and can be at least partially resorbable. In one embodiment, the base component includes a plurality of circumferentially extending ridges.

The base component can be made of a composite material, a dispersion of collagen and a calcium composition. The calcium composition can be selected from tricalcium phosphate, hydroxyapatite, or a combination of tricalcium phosphate and hydroxyapatite. In one embodiment, the dispersion includes about 90% by weight calcium composition and about 10% by weight collagen.

The details of one or more embodiments of the invention are set forth in the accompanying description above. Although any methods and materials similar or equivalent to those described herein can be used in the practice or testing of the invention, the preferred methods and materials are now described. Other features, objects, and advantages of the invention will be apparent from the description and from the claims. In the specification and the appended claims, the singular forms include plural referents unless the context clearly dictates otherwise. Unless defined otherwise, all technical and scientific terms used herein have the same meaning as commonly understood by one of ordinary skill in the art to which this invention belongs. All patents and publications cited in this specification are incorporated by reference.

The following EXAMPLES are presented to more fully illustrate the preferred embodiments of the invention. The EXAMPLES should in no way be construed as limiting the scope of the invention, as defined by the appended claims.

EXAMPLE 1

Device I Fabrication (A) Approximately 700 g of a Type I collagen dispersion (treated with $\alpha$-galactosidase to eliminate $\alpha$-Gal epitopes) is weighed into a 2 liter vacuum flask. Approximately 120 ml 0.66 ammonium hydroxide is added to the dispersion to coacervate the collagen. About 80 ml 20% NaCl is then added to the coacervated fibers to further reduce the solution imbibition between the fibers.

(B) The fully coacervated fibers are dehydrated to about 70 g to 80 g in a perforated mesh basket to remove the excess solution from the fibers.

(C) The partially dehydrated collagen fibers are inserted into a mold of specified dimension related to the dimensions of the defect to be remedied. Further dehydration is ongoing in the mold using a constant (between 300 grams to 700 grams) weight to slowly remove the water from the fibers, yet maintaining the same density throughout. This slow dehydration process lasts for about 24 hours until the desired dimension (about 8 mm in thickness) is reached.

(D) The dehydrated collagen matrix is further shaped to the desired form figure.

(E) The dehydrated collagen fibers are frozen at $-20°$ C. for at least 4 hours before freeze drying in a Virtis® freeze dryer.

(F) The frozen collagen fibers are first dried at $-10°$ C. for 48 to 72 hours, followed by drying at $20°$ C. for 16 to 24 hours at a vacuum of 400 millibar.

(G) The freeze dried matrices are subjected to a formaldehyde cross-linking procedure. The matrices are cross-linked for 40 hours in a closed chamber of formaldehyde vapor generated from a 2% formaldehyde solution at $22°$ C. The cross-linked matrices are vented extensively to remove the non-bounded formaldehyde.

(H) The matrices are then subjected to a heat and vacuum treatment to further cross-link the matrices.

(I) The matrices are cut to the shape of the segmental defect of the meniscus to be repaired. The cut matrices are extensively rinsed in pyrogen free distilled water to remove the residual salts and formaldehyde to the extent that the matrices are biocompatible in vitro and in vivo.

(J) The rinsed matrices are dried under a hepafilter and are packaged and sterilized.

EXAMPLE 2

Device II Fabrication

The procedure for fabricating Device II is identical to that described in Example 2, except that approximately 700 g of a Type II collagen dispersion (treated with $\alpha$-galactosidase to eliminate $\alpha$-Gal epitopes) are used.

EXAMPLE 3

Device III Fabrication (A) The collagen content of the highly purified type I collagen fibrils (treated with $\alpha$-galactosidase to eliminate $\alpha$-Gal epitopes) is determined either by gravimetric methods or by determining the hydroxyproline content assuming a 13.5% by weight of hydroxyproline in Type I collagen. The amount of purified material needed to fabricate a given density of a meniscal augmentation device is then determined and weighed.

(B) A solution of fibrillar collagen is fit into a mold of specified dimensions, e.g., according to the exemplary meniscal augmentation devices described above. Collagen fibers are laid down in random manner or in an oriented manner. In the oriented manner, circumferential orientation of the fibers is produced by rotation of the piston about its principal axis as the material is compressed in the mold; radial orientation is produced by manual painting of the collagen fibers in a linear, radially directed fashion.

(C) The fibers are frozen at $-20°$ C., turned out of the mold, and thawed at room temperature.

(D) The fibers are then resuspended in phosphate buffered saline, put back into the mold in the desired orientations, and compressed with the piston.

(E) The compressed fibers are then refrozen $-20°$ C. and then thawed at room temperature.

(F) The resulting structure is cross-linked by soaking in a 0.2% glutaraldehyde solution, pH 7.6 for 24 ($\pm 0.5$) hours. Each glutaraldehyde-cross-linked meniscal augmentation device is subsequently rinsed repeatedly in 500 ml of phosphate buffered saline (PBS) solution, pH 7.4, for 4, 8, 24, and 48 hours.

(G) The rinsed matrix is then lyophilized.

EXAMPLE 4

Assessment of Primate Response to Implanted Prosthetic Menisci Treated with A-Galactosidase In this EXAMPLE, matrix material for prosthetic devices is treated with α-galactosidase to eliminate α-galactosyl epitopes, the implants are transplanted into cynomolgus monkeys and the primate response to the soft tissue implants is assessed.

Each set of matrix material is cut into two portions. Each first portion is immersed in a buffer solution containing α-galactosidase at a predetermined concentration. The specimens are allowed to incubate in the buffer solutions for a predetermined time period at a predetermined temperature. Each second portion is incubated under similar conditions as the corresponding first portion in a buffer solution in the absence of α-galactosidase and serves as the control.

At the end of the incubation, the matrix materials are washed under conditions that allow the enzyme to diffuse out. Assays are performed to confirm the complete removal of the α-gal epitopes.

Each prosthetic device is implanted in the supra patellar pouch of six cynomolgus monkeys. With the animals under general inhalation anesthesia, an incision of about 1 cm is made directly into the supra patellar pouch at the superior medial border of the patella extending proximally.

Prosthetic devices are also implanted in six cynomolgus monkeys using the following implantation procedure. With the animals under general inhalation anesthesia, the anatomic insertion sites for the prosthetic devices are identified and drilled to Accommodate a substantially 9 mm in diameter by 40 mm in length bone plug. The prosthetic device is brought through the drill holes and affixed with interference screws.

The implantation procedures are performed under sterile surgical technique, and the wounds are closed with 3-0 vicryl or a suitable equivalent known to those of ordinary skill in the art. The animals are permitted unrestricted cage activity and monitored for any sign of discomfort, swelling, infection, or rejection. Blood samples (e.g., 2 ml) are drawn periodically (e.g., every two weeks) for monitoring of antibodies.

The occurrence of an immune response against the prosthetic device is assessed by determining anti-Gal and non-anti-Gal anti-soft tissue antibodies (i.e., antibodies binding to soft tissue antigens other than the α-gal epitopes) in serum samples from the transplanted monkeys. At least two ml blood samples are drawn from the transplanted monkeys on the day of implant surgery and at periodic (e.g., two week) intervals post-transplantation. The blood samples are centrifuged and the serum samples are frozen and evaluated for the anti-Gal and other antibody activity.

Anti-Gal activity is determined in the serum samples in ELISA with α-gal-BSA as solid phase antigen, according to methods known in the prior art, such as, for example, the methods described in Galili et al., *Transplantation* 63: 645-651 (1997).

Assays are conducted to determine whether α-galactosidase treated prosthetic devices induce the formation of anti-soft tissue antibodies. For measuring anti-soft tissue antibody activity, ELISA assays are performed according to methods known in the prior art, such as, for example, the methods described in K. R. Stone et al., *Transplantation* 63: 640-645 (1997).

The prosthetic devices are optionally explanted at one to two months post-transplantation, sectioned and stained for histological evaluation of inflammatory infiltrates. Post-transplantation changes in anti-Gal and other anti-cartilage soft tissue antibody activities are correlated with the inflammatory histologic characteristics (i.e., granulocytes or mononuclear cell infiltrates) within the prosthetic device, one to two months post-transplantation, using methods known in the art, as, for example, the methods described in K. R. Stone et al., *Transplantation* 63: 640-645 (1997).

The animals that have had prosthetic devices implanted are allowed to recover and are monitored closely until the incisions have healed and the gait is normal. The prosthetic devices are collected, processed, and examined microscopically.

Portions of the prosthetic devices and surrounding tissues are frozen in embedding mediums for frozen tissue specimens in embedding molds for immunohistochemistry evaluation according to the methods known in the prior art. "TISSUE-TEK®" O.C.T. compound which includes about 10% w/w polyvinyl alcohol, about 4% w/w polyethylene glycol, and about 86% w/w nonreactive ingredients, and is manufactured by Sakura FinTek® (Torrence, Calif., USA) is a non-limiting example of a possible embedding medium for use with the invention. Other embedding mediums known to those of ordinary skill in the art may also be used. The remaining implant and surrounding tissue is collected in 10% neutral buffered formalin for histopathologic examination.

EXAMPLE 5

Assay for A-Gal Epitopes' Elimination from Matrix Material by A-Galactosidase

In this example an ELISA assay for assessing the elimination of α-gal epitopes from matrix material is conducted.

Assay For α-Galactosidase. The enzyme α-galactosidase (previously cloned from coffee beans and genetically expressed in the yeast *Pichia pastoris*) has been well-characterized (Zhu et al., *Arch. Biochem. Biophysics* 324: 65 (1995)). α-galactosidase is an exoglycosidase of molecular weight 41 kDa that is diffusely distributed in nature. It functions by cleaving the terminal α-galactose residue from oligosaccharide chains from cells. The activity of recombinant enzyme is determined by reacting diluted enzyme with p-nitrophenyl-α-galactoside substrate, for 10 minutes at room temperature (Zhu et al., *Arch. Biochem. Biophysics* 827:324 (1996)). The absorbance of p-nitrophenol in each solution is read at 405 nm. The enzyme is stable at 37° C., 24° C., and 4° C., and is affected by repeated freezing and thawing. The activity of each batch of enzyme is checked prior to use in assays.

A monoclonal anti-Gal antibody (designated M86) which is highly specific for α-gal epitopes on glycoproteins is produced by fusion of splenocytes from anti-Gal producing knock-out mice for α 1,3-galactosyltransferase, and a mouse hybridoma fusion partner.

M86 binds to synthetic α-gal epitopes linked to bovine serum albumin (BSA), to bovine thyroglobulin which has 11 α-gal epitopes, R. G. Spiro et al., *J. Biol. Chem.* 259: 9858 (1984); or to mouse laminin which has 50 α-gal epitopes, R. G. Arumugham et al., *Biochem. Biophys. Acta* 883: 112 (1986); but not to human thyroglobulin or human laminin, Galβ1-4 GlcNAc-BSA (N-acetyllactosamine-BSA) and Galα1-4Galβ1-4GlcNAc-BSA (P1 antigen linked to BSA), all of which completely lack α-gal epitopes.

Once the M86 antibody is isolated, the monoclonal antibody is diluted from about 1:20 to about 1:160, and preferably diluted from about 1:50 to about 1:130. The antibody is incubated for a predetermined period of time ranging between about 5 hr to about 24 hr, at a predetermined temperature ranging from about 3° C. to about 8° C. The antibody is maintained in constant rotation with fragments of soft tissue about 5 μm to about 100 μm in size, and more preferably with soft tissue fragments ranging from about 10 μm to about 50 μm in size, at various soft tissue concentrations ranging from about 200 mg/ml to about 1.5 mg/ml. Subsequently, the soft tissue fragments are removed by centrifugation at centrifugation rate ranging from about 20,000×g to about 50,000×g. The proportion of M86 bound to the soft tissue is assessed by measuring the remaining M86 activity in the supernatant, in ELISA with α-gal-BSA as described in the prior art in, for example, U. Galili et al., *Transplantation* 63: 645-651 (1997). The extent of binding of M86 to the soft tissue is defined as a percentage inhibition of subsequent binding to α-gal-BSA. There is a direct relationship between the amount of α-gal epitopes in the matrix material and the proportion of M86 complexed with the matrix material fragments, thus removed from the supernatant (i.e., percentage inhibition).

Determination of Enzyme Protein Concentration-Specific Activity Determination. This assay employs the Sigma Diagnostics Microprotein-PR™ kit that quantitatively determines the amount of protein in solution. The reaction medium consists of 0.05 mmol/L pyrogallol red, 0.16 mmol/L sodium molybdate. The protein standard solution consists of human albumin (50 mg/100 ml) in saline with 0.1% sodium azide as a preservative. 95 μl of the pyrogallol reagent is added into each well. Deionized water is used as a blank. Into the test wells are added 5 μl of enzyme solution (1/50 dilution). The standard albumin solution is added into separate wells. The multiwell plate and contents is incubated for 3 minutes at 37° C. The absorbance is determined at 600 nm. The protein concentration is calculated using the formula: Protein (mg/dl)=$A_{test}-A_{blank}/A_{standard}-A_{blank}$ X Concentration of Standard.

The foregoing description has been presented only for the purposes of illustration and is not intended to limit the invention to the precise form disclosed, but by the claims appended hereto.

What is claimed is:

1. A substantially non-immunogenic prosthetic device for implantation into a vertebrate subject in a region disposed between and connecting two of the subject's bones, comprising a biocompatible glycosidase-treated matrix material, wherein the device matrix is adapted to have an in vivo an outer surface contour substantially the same as that of region disposed between and connecting two of the subject's bones, wherein the device is a prosthetic ligament comprising a plurality of substantially aligned, elongated filaments,
   (a) wherein the fibrils are present in the matrix at a concentration of about 75 to 100% by dry weight, and
   (b) wherein polysaccharide molecules in the matrix are present at a concentration of about 0 to 25% by dry weight.

2. A substantially non-immunogenic prosthetic device for implantation into a vertebrate subject in a region disposed between and connecting two of the subject's bones, comprising a biocompatible glycosidase-treated matrix material, wherein the device matrix is adapted to have an in vivo an outer surface contour substantially the same as that of a region disposed between and connecting two of the subject's bones wherein the device is a prosthetic articular cartilage device adapted to have an in vivo outer surface contour substantially the same as that of natural articular cartilage further comprising a biocompatible conical base component including an anchor for anchoring the articular cartilage device in a complimentary aperture in cancellous bone, the base component extending from portions of the outer surface of the matrix.

3. The device of claim 2, wherein the base component is at least partially resorbable.

4. The device of claim 2, wherein the base component includes a plurality of circumferentially extending ridges.

5. The device of claim 2, wherein the base component is composed of a composite material, comprising:
   (a) a dispersion of collagen and a
   (b) composition which is selected from the group consisting of tricalcium phosphate hydroxyapatite, and a combination of tricalcium phosphate and hydroxyapatite.

6. The device of claim 5, wherein the dispersion comprises about 90% by weight tricalcium phosphate and about 10% by weight collagen.

7. The device of claim 5, wherein the dispersion comprises about 90% by weight hydroxyapatite and about 10% by weight collagen.

* * * * *